United States Patent [19]
Futatsugi et al.

[11] Patent Number: 5,834,273
[45] Date of Patent: *Nov. 10, 1998

[54] HEAT-STABLE AND WATER SOLUBLE MODIFIED ENZYMES

[75] Inventors: Masayuki Futatsugi; Kenji Gushi, both of Amagasaki, Japan

[73] Assignee: Wako Pure Chemical Industries, Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 266,097

[22] Filed: Jun. 24, 1994

Related U.S. Application Data

[63] Continuation of Ser. No. 857,424, Mar. 26, 1992, abandoned.

[30] Foreign Application Priority Data

Mar. 28, 1991  [JP]  Japan ................................. 3-089697

[51] Int. Cl.$^6$ ............................... C12N 9/02; C12N 9/04; C12N 9/06
[52] U.S. Cl. ........................... 435/177; 435/190; 435/191
[58] Field of Search ..................... 435/174, 178, 435/180, 181, 190, 191

[56] References Cited

U.S. PATENT DOCUMENTS

| | | | |
|---|---|---|---|
| 4,003,792 | 1/1977 | Mill ........................................... | 424/12 |
| 4,585,754 | 4/1986 | Meisner et al. . | |
| 4,652,524 | 3/1987 | Modrovich .............................. | 435/188 |
| 4,716,103 | 12/1987 | Hunger et al. .......................... | 435/174 |
| 4,845,038 | 7/1989 | Fanta et al. ............................. | 435/178 |
| 4,910,135 | 3/1990 | Tischer ..................................... | 435/28 |
| 4,940,664 | 7/1990 | Mücke ..................................... | 435/174 |
| 4,950,609 | 8/1990 | Tischer et al. .......................... | 435/174 |
| 4,968,495 | 11/1990 | Inoue et al. ............................. | 435/178 |

FOREIGN PATENT DOCUMENTS

| | | |
|---|---|---|
| 0 049 475 | 4/1982 | European Pat. Off. . |
| 29 19 622 | 11/1980 | Germany . |
| 1-128786 | 5/1989 | Japan . |
| 2-231075 | 9/1990 | Japan . |
| 2-231076 | 9/1990 | Japan . |
| 2-231077 | 9/1990 | Japan . |
| 2-231078 | 9/1990 | Japan . |
| 3-147784 | 6/1991 | Japan . |

OTHER PUBLICATIONS

Gordon, C.N., *Adv. Exp. Med. Biol.*, 86A, pp. 649–656 1977.
Yasuda et al., Chem. Pharm. Bull., 38(7), pp. 2053–2056 (1990.
Fox et al (1978) Infection and Immunity 20, pp. 867–868.
Beddows et al (1984) Biotechnology and Bioengineering 27, pp. 580–587.
Nature, vol. 214, pp. 1302–1304 Jun. 24, 1967.
Journal of Solid–Phase Biochemistry, vol. 4, No. 4 pp. 233–243, 1979.
Proc. Natl. Acad. Science USA, vol. 73, No. 6, pp. 2128–2131, Jun. 1976.
Abstracts: World Patents Index Latest Week 9117, Derwent Publications Ltd., London, GB; AN 91–120502 & JP–A–3 058 783 (Wako Pure Chem Ind KK) 13 Mar. 1991.
Abstract No. 67920S Chemical Abstracts, vol. 98, No. 9, 28 Feb. 1983, "Immobilization of Urease on Synthetic Polymers", and Biotechnol. Bioeng. 1982, vol. 24, No., 12, pp. 2757–2763.
Patent Abstracts of Japan, vol. 7, No. 181 (C–180) 10 Aug. 1983 and JP–A–58 086 083 (Wako Junyaku Kogyo KK) 23 May 1983.

*Primary Examiner*—Irene Marx
*Attorney, Agent, or Firm*—Armstrong, Westerman, Hattori, McLeland & Naughton

[57] ABSTRACT

A modified enzyme obtained by modifying an enzyme such as a hydrogen peroxide-generating enzyme, ascorbate oxidase, etc. with a polysaccharide, polyamino acid or synthetic polymer having a plurality of carboxyl groups via a crosslinking agent capable of binding both carboxyl group and amino group is remarkably improved in resistance to heat, proteases, etc. and in storage stability in an aqueous solution.

8 Claims, 3 Drawing Sheets

F I G. 2
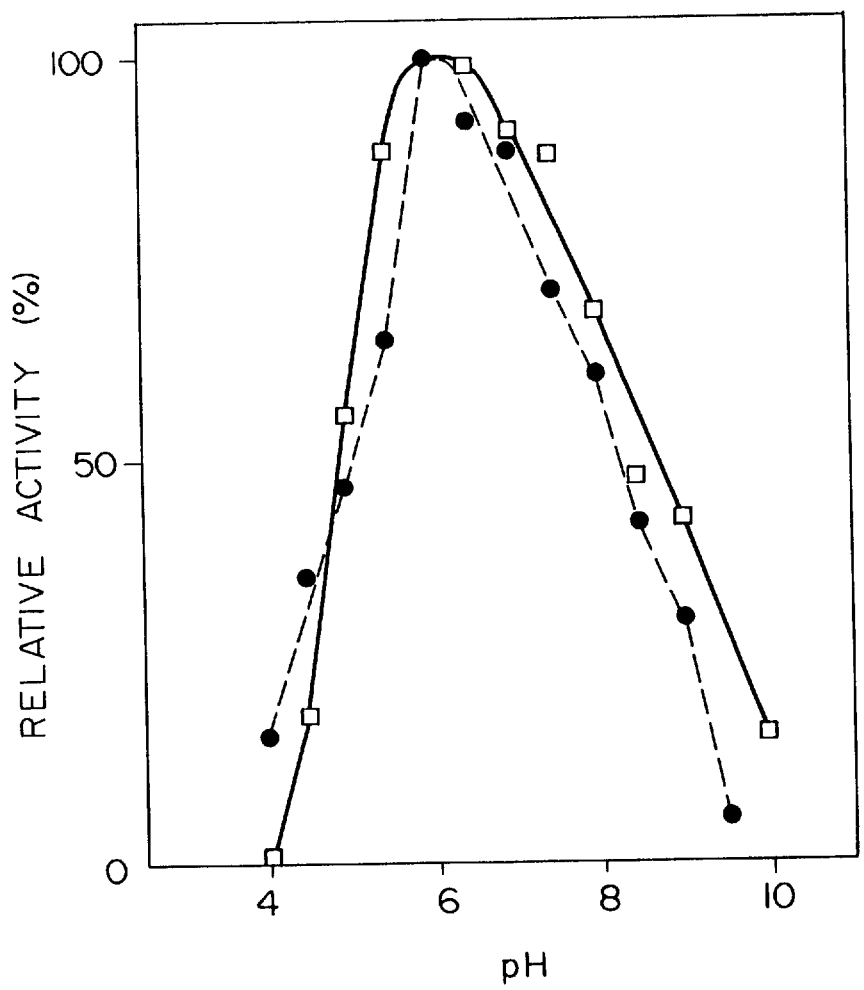

HEAT-STABLE AND WATER SOLUBLE MODIFIED ENZYMES

This application is a continuation of application Ser. No. 07/857,424 filed Mar. 26, 1992, now abandoned.

BACKGROUND OF THE INVENTION

This invention relates to a modified enzyme remarkably improved in stability in an aqueous solution.

Recently, noticing excellent catalytic function, effective applications of enzymes outside of living bodies have been tried actively. For example, various methods for measuring micro-components applying catalytic reactions of enzymes are widely practiced in the fields of clinical chemistry, biochemistry, food chemistry, food industry, and the like. But the enzymes used in these measuring methods are low in stability in aqueous solutions. Thus, the usable time of prepared enzyme solutions is short. In order to use effectively, it is necessary to prepare such aqueous enzyme solutions at the time of use in necessary amounts.

In order to improve the stability of enzymes in aqueous solutions, there have been proposed various methods, for example, a method of adding as a stabilizing agent for enzymes a saccharide such as sucrose, maltose, etc., a protein such as albumin, skim milk, etc., a salt such as $Ca^{2+}$, $Mg^{2+}$, etc., a reducing agent such as 2-mercaptoethanol, etc., a polyol such as polyethylene glycol, etc., a substrate of enzyme, a coenzyme, a chelating agent, etc.; a method of fixing an enzyme on a suitable carrier; a method of modifying amino acid sequence of an enzyme by means of genetic engineering; etc. Since there is no general rule which method is suitable for a specific enzyme, a stabilizing method is selected for individual enzymes by trial and error. Among these stabilizing methods, the method of fixing on a carrier is frequently used recently and known as a method having a relatively high stabilizing effect (German Patent No. 2,919,622, etc.). But even this method has a problem in that when an active center of enzyme or an amino acid residue relating to expression of enzymatic activity such as a substrate binding site is modified, the enzymatic activity is not expressed. Thus, even if a binding method, a binding agent, a crosslinking agent, and the like are studied for selecting the best conditions, such conditions are not always applicable for every enzyme as in the other methods.

On the other hand, in order to solve the above mentioned problems, there is also proposed a method of screening enzymes, which are good in stability in an aqueous solution and have properties suitable for quantitatively determining the desired microcomponents in living body samples, from various microorganisms such as thermophilic bacteria. But this method not only requires much money and time but also gives no guarantee for finding precisely enzymes suitable for the purpose. Thus, this method is not a usable method.

SUMMARY OF THE INVENTION

It is an object of the present invention to provide a modified enzyme remarkably improved in stability in an aqueous solution overcoming the problems mentioned above.

The present invention provides a modified enzyme comprising an enzyme selected from the group consisting of an enzyme generating hydrogen peroxide, ascorbate oxidase, peroxidase, urease, catalase, and glycerokinase bound to a polysaccharide having a plurality of carboxyl groups a polyamino acid having a plurality of carboxyl groups or a synthetic polymer having a plurality of carboxyl groups via a crosslinking agent capable of binding a carboxyl group and an amino group.

BRIEF DESCRIPTION OF THE DRAWINGS

FIG. 2 is a graph showing pH activity curves obtained in Experiment 3.

DESCRIPTION OF THE PREFERRED EMBODIMENTS

Figure 1:
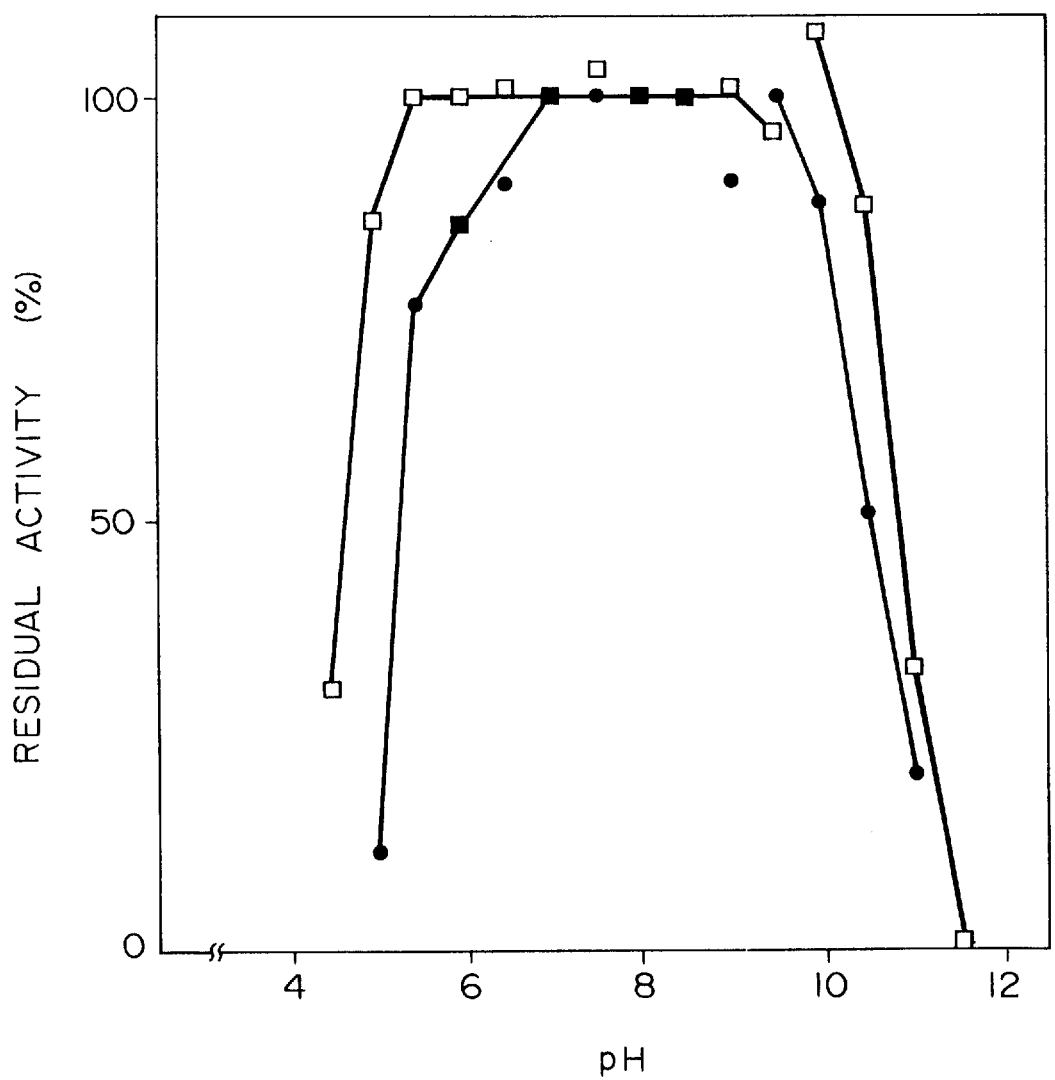
FIG. 1 is a graph showing pH stability curves obtained in Experiment 3.

According to the present invention, an enzyme to be modified by binding a polysaccharide having a plurality of carboxyl groups, a polyamino acid having a plurality of carboxyl groups or a synthetic polymer having a plurality of carboxyl groups via a crosslinking agent capable of binding a carboxyl group and an amino group, is selected from the group consisting of an enzyme generating hydrogen peroxide, ascorbate oxidase (E.C.1.10.3.3, hereinafter referred to as "AOD"), peroxidase (E.C.1.11.1.7, hereinafter referred to as "POD"), urease (E.C.3.5.1.5, hereinafter referred to as "URS"), catalase (E.C.1.11.1.6, hereinafter referred to as "CAT"), and glycerokinase (E.C.2.7.1.30, hereinafter referred to as "GK"). The modified enzyme is remarkably high in stability in an aqueous solution and excellent in resistance to heat, proteases, modifying agents, and has the same fundamental properties such as Km values, optimum pH range, etc., at the time of enzymatic reaction as the non-modified enzymes.

As the enzyme generating hydrogen peroxide, there can be used enzymes which generate hydrogen peroxide by reaction with a substrate. Preferable examples of such enzymes are choline oxidase (E.C.1.1.3.17, hereinafter referred to as "COD"), glucose oxidase (E.C.1.1.3.4, hereinafter referred to as "GOD"), xanthine oxidase (E.C.1.2.3.2, hereinafter referred to as "XOD"), oxalate oxidase (E.C.1.2.3.4, hereinafter referred to as "OOD"), sarcosine oxidase (E.C.1.5.3.1, hereinafter referred to as "SAO"), uricase (E.C.1.7.3.3, hereinafter referred to as "US"), etc.

Further, the origin of the enzyme generating hydrogen peroxide, AOD, POD, URS, CAT and GK is not particularly limited and any ones derived from animals, plants, microorganisms can be used. Further, the purity of enzymes is not a problem particularly. Needless to say, it is preferable not to contain proteases.

As the crosslinking agent capable of binding a carboxyl group and an amino group, there can be used compounds which can bind a carboxyl group and an amino group. Preferable examples of the crosslinking agent are carbodiimide, carbodiimide derivatives such as dicyclohexylcarbodiimide, di-p-toluoylcarbodiimide, benzyldimethylaminopropylcarbodiimide (BDC), 1-ethyl-3-(3-dimethylaminopropyl)carbodiimide (WSC), etc.; Woodward reagent, etc.

As the polysaccharide having a plurality of carboxyl groups, the polyamino acid having a plurality of carboxyl groups, or a synthetic polymer having a plurality of carboxyl groups, there can be used natural polysaccharides having carboxyl groups such as alginic acid, pectic acid, protuberic acid, hyaluronic acid, chondroitin, heparin, etc.; polysaccharides introducing carboxyl groups thereinto artificially such as carboxymethyl cellulose, carboxymethyl dextran, etc.;

polyamino acids such as polyglutamic acid, polyaspartic acid, polyamino acids containing a plurality of glutamic acid residues and/or a plurality of aspartic acid residues, etc.; synthetic polymers such as ethylene-maleic acid copolymer, methylvinylether-maleic acid copolymer, styrene-maleic acid copolymer, etc.

As the polysaccharides introducing carboxyl groups thereinto artificially, there can also be used those obtained by activating a polysaccharide such as dextran, dextran sulfate, pullulan, Ficoll, starch, dextrin, cellulose, α-cyclodextrin, β-cyclodextrin, γ-cyclodextrin, or the like by a method using cyanogen bromide (Nature, vol. 214, page 1302, 1967), epichlorohydrine (Infect. Immun., vol. 20, page 867, 1978), 1-cyano-4-dimethylaminopyridinium salt, 2,4,6-trichloro-1,3,5-triazine (J. Solid-Phase Biochem., vol. 4, page 233, 1979), or periodic acid (Proc, Natl. Acod. Sci. U.S.A., vol. 73, page 2128, 1976), followed by reaction with an amino acid. As the amino acid, there can be used compounds having one or more amino groups and one or more carboxyl groups. Preferable examples of such amino acids are β-alanine, 4-aminobutyric acid, 5-aminovaleric acid, 6-aminocaproic acid, p-aminophenyl-acetic acid, p-aminobenzoic acid, glutamic acid, aspartic acid, etc.

Further, as the polysaccharides introducing carboxyl groups thereinto artificially, there can also be used those obtained by reacting the polysaccharides mentioned above directly with an acid anhydride such as maleic anhydride, succinic anhydride, phthalic anhydride, pyromellitic anhydride, mellitic anhydride, trimellitic anhydride, etc.

The direct reaction with an acid anhydride is explained in detail below.

To a solution obtained by dissolving a polysuccharide in a solvent such as water, a pyro-phosphate buffer, etc. containing no amine so as to make the concentration usually 0.5 to 10% by weight, preferably 4 to 8% by weight, an acid anhydride such as maleic anhydride, succinic anhydride, phthalic anhydride, pyromellitic anhydride, mellitic anhydride or trimellitic anhydride is added gradually in a suitable amount while maintaining the pH usually at 7 to 10, preferably 8 to 9 using a pH-stat. After the addition, stirring is continued until the pH of reaction solution does not vary. Then, the reaction solution is desalted by dialysis, gel filtration, etc., followed by concentration or freeze drying to obtain the desired polysaccharide introducing carboxyl groups thereinto artificially. According to this process, carboxyl groups can be introduced into all the hydroxyl groups in the starting polysaccharide. By properly selecting and adjusting the kind and amount of acid anhydride, the introduced amount of carboxyl group can be adjusted. Thus, the kinds and molar ratio of the polysaccharide and acid anhydride can be selected properly depending on purposes.

The molecular weight of polysaccharide into which carboxyl groups are to be introduced is usually about 4,000 to 10,000,000, preferably 10,000 to 500,000.

In the case of polysaccharide, the amount of carboxyl group is usually 0.1 to 5, preferably 0.2 to 4, more preferably 2 to 4 per constituting sugar unit (glucose residue, glucosamine residue, etc.). On the other hand, in the case of polyamino acid, it is preferable to use that having glutamic acid residue and/or aspartic acid residue in an amount of 25% or more as the amino acid residue. In the case of the synthetic polymer, it is preferable to use the polymer having the constituting unit containing carboxyl groups in an amount of 25% or more based on the total weight of the polymer.

The modified enzyme can be synthesized as follows. A suitable amount of polysaccharide having a plurality of carboxyl groups, polyamino acid having a plurality of carboxyl groups or synthetic polymer having a plurality of carboxyl groups (hereinafter referred to as "carboxy high polymer") is dissolved in water or a buffer solution such as a phosphate buffer, quinoline buffer, etc., followed by addition of a crosslinking agent in an amount of usually 1 to 10 equivalent weight, preferably 3 to 7 equivalent weight per equivalent weight of the carboxyl group in the carboxy high polymer. Then, an enzyme to be modified is added to the solution in an amount of preferably 0.1 to 10 parts by weight, more preferably 0.5 to 3 parts by weight per part by weight of the carboxy high polymer. The reaction is carried out at a pH of preferably 4.0 to 8.0, more preferably 5.0 to 7.5 using a pH-stat or the like and preferably 1° to 40° C., more preferably 4° to 30° C. for preferably 1 to 48 hours, more preferably 10 to 24 hours. After the reaction, the reaction solution is purified by dialysis, gel filtration, or the like to obtain the modified enzyme of the present invention. Needless to say, the purification to obtain the modified enzyme having desired molecular weight can be carried out by gel filtration chromatography, etc.

The modified enzyme of the present invention has almost the same fundamental properties at the time of enzymatic reaction such as Km values, optimum pH range, etc. as the original enzyme, and is remarkably improved in resistance to heat, proteases, denaturants, etc. and in storage stability in aqueous solutions. Therefore, when a diagnostic reagent is prepared using the modified enzyme of the present invention, the resulting diagnostic reagent is not only usable for a long period of time in the form of solution but also able to be reduced in initial changing amount of enzyme due to almost no change in enzymatic activity.

The modified enzyme of the present invention can be stored as a freeze dried product, which has good solubility when dissolved at the time of use.

The present invention is illustrated by way of the following Examples and Experiments, in which all percents are by weight unless otherwise specified.

In the following Examples and Experiments, the enzymatic activity was measured as follows:

Measuring Method of AOD Activity (Substrate solution)

A substrate solution was prepared by dissolving 140 mM of ascorbic acid in 50 mM of phosphate buffer (pH 5.6).

(Measuring procedure)

After well mixing 3.0 ml of a substrate buffer solution previously preheated at 25° C. with 40 μl of a sample, a change of absorbance at 295 nm of the resulting solution was measured using a spectrophotometer controlled at 25° C. AOD activity was obtained by inserting the obtained changing rate of absorbance per minute (ΔE) into the following equation (1):

$$\text{AOD activity } (U/ml) = 3.04 \div 2.67 \div 0.04 \times \Delta E \qquad (1)$$

Measuring Method of COD Activity

The method described in Method of Enzymatic Analysis, vol. 2, pages 172–173, 1983.

Measuring Method of GK Activity

The method described in Method of Enzymatic Analysis, vol. 2, pages 216–217, 1983.

Measuring Method of GOD Activity

The method described in Method of Enzymatic Analysis, vol. 2, pages 201–202, 1983.

Measuring Method of US Activity

The method described in Method of Enzymatic Analysis, vol. 3, pages 500, 1963.

Measuring Method of SAO Activity

The method described in Method of Enzymatic Analysis, vol. 17A, pages 976, 1970.

Measuring Method of XOD Activity

The method described in Method of Enzymatic Analysis, vol. 3, pages 212, 1983.

EXAMPLE 1

Preparation of Modified AOD (1) In 20 ml of 0.2M pyrophosphate buffer solution (pH 9.0), 1 g of dextran (molecular weight 100,000 to 200,000) was dissolved. To the resulting solution, 6 g of pyromellitic anhydride was added gradually while maintaining the pH of the solution at 8 to 9 using a pH-stat. Then, the reaction was continued at room temperature with stirring for 2 hours. The resulting reaction solution was placed in a dialysis tube and dialyzed against water (3 liters×5 times) to obtain pyromellitic acid-modified dextran. The amount of carboxyl group in the pyromellitic acid-modified dextran was 3.0 per glucose residue constituting the pyromellitic acid-modified dextran.

(2) A solution obtained by dissolving 10 mg of AOD (mfd. by Eastman Kodak Co., drived from cucumber) in 1 ml of 5 mM of phosphate buffer solution (pH 6.0) and dialyzed against a phosphate buffer solution several times. The resulting solution was added to a solution obtained by adding 180 mg of WSC (1-ethyl-3-(3-dimethyl-aminopropyl) carbodiimide) to 6 ml of 20 mM phosphate buffer solution containing 10 mg of pyromellitic acid-modified dextran obtained in (1) mentioned above with stirring, followed by reaction at 5° C. for 24 hours. The resulting reaction solution was placed in a dialysis tube and dialyzed against 20 mM phosphate buffer solution (pH 7.0) to obtain the desired modified AOD (enzymatic activity recovery 65%). When the resulting modified AOD was analyzed by using high-pressure liquid chromatography (HPLC), the molecular weight was about 700,000. Further, unreacted AOD was hardly observed.

Experiment 1

Study of Thermal Stability

Thermal stability of the modified AOD obtained in Example 1 and the intact AOD was compared.

(Procedure)

In 20 mM phosphate buffer solution (pH 7.0), predetermined AOD was dissolved so as to make the amount 5 U/ml, and stored at predetermined temperatures for 10 minutes, followed by rapid cooling. A change of AOD activity before and after treatment was measured.

(Results)

The results are shown in Table 1.

TABLE 1

| Treating temperature (°C.) | Residual activity (%) | |
|---|---|---|
| | Modified AOD | Intact AOD |
| 50 | 100 | 100 |
| 55 | 100 | 100 |
| 60 | 100 | 22.3 |
| 65 | 100 | 3.2 |
| 70 | 100 | 0 |
| 75 | 93.4 | 0 |
| 80 | 41.5 | 0 |

The figures in Table 1 mean residual activity when AOD activity before treatment is taken as 100.

As is clear from the results of Table 1, the modified AOD of the present invention is remarkably improved in thermal stability compared with the intact AOD.

Experiment 2

Study of Storage Stability in Solution

Storage stability in a solution of the modified AOD obtained in Example 1 and the intact AOD was compared.

(Procedure)

In 20 mM phosphate buffer solution (pH 7.0), predetermined AOD was dissolved so as to make the amount 5 U/ml, and stored at predetermined temperatures for predetermined days. A change of AOD activity was measured.

(Results)

The results are shown in Table 2.

TABLE 2

| Stored temperature | Residual activity (%) | | | | | |
|---|---|---|---|---|---|---|
| | 4° C. | | 30° C. | | 45° C. | |
| Stored days | Modified AOD | Intact AOD | Modified AOD | Intact AOD | Modified AOD | Intact AOD |
| 2 | — | — | — | — | 100 | 69.8 |
| 5 | — | — | — | — | 100 | 15.4 |
| 10 | — | — | 94.0 | 89.2 | 89.1 | 7.9 |
| 15 | 99.8 | 91.8 | — | — | 50.2 | 0 |
| 20 | — | — | 81.2 | 69.5 | 40.5 | 0 |
| 30 | — | — | 77.0 | 59.7 | — | — |
| 50 | 99.9 | 81.8 | 70.0 | 25.4 | — | — |
| 80 | — | — | 34.3 | 2.9 | — | — |
| 90 | 92.3 | 75.1 | — | — | — | — |
| 110 | 90.1 | 72.7 | — | — | — | — |
| 141 | 90.5 | 73.3 | — | — | — | — |

The figures in Table 2 mean residual activity after predetermined days when AOD activity immediately after the preparation of AOD solution is taken as 100.

As is clear from the results of Table 2, the storage stability in the solution of the modified AOD of the present invention is remarkably improved compared with the intact AOD.

Experiment 3

Study of Resistance to Denaturant

Resistance to a denaturant (urea) of the modififed AOD obtained in Example 1 was compared with the intact AOD.

(Procedure)

In a urea solution with a predetermined concentration, predetermined AOD was dissolved so as to make the amount 5 U/ml, and stored at 30° C. for 16 hours. A change of AOD activity was measured.

(Results)

The results are shown in Table 3. In Table 3, the figures mean the residual activity after treatment with the denaturant, when the AOD activity immediately after the preparation of the AOD solution is taken as 100.

TABLE 3

| Concentration of urea (M) | Residual activity (%) | |
|---|---|---|
| | Modified AOD | Intact AOD |
| 0 | 100 | 100 |
| 2 | 100 | 88.4 |
| 3 | 100 | 44.6 |
| 4 | 100 | 5.5 |
| 6 | 45.6 | 0 |
| 8 | 3.0 | 0 |

As is clear from the results of Table 3, the modified AOD of the present invention is remarkably improved in resistance to the denaturant (urea) compared with the intact AOD.

Figure 3:
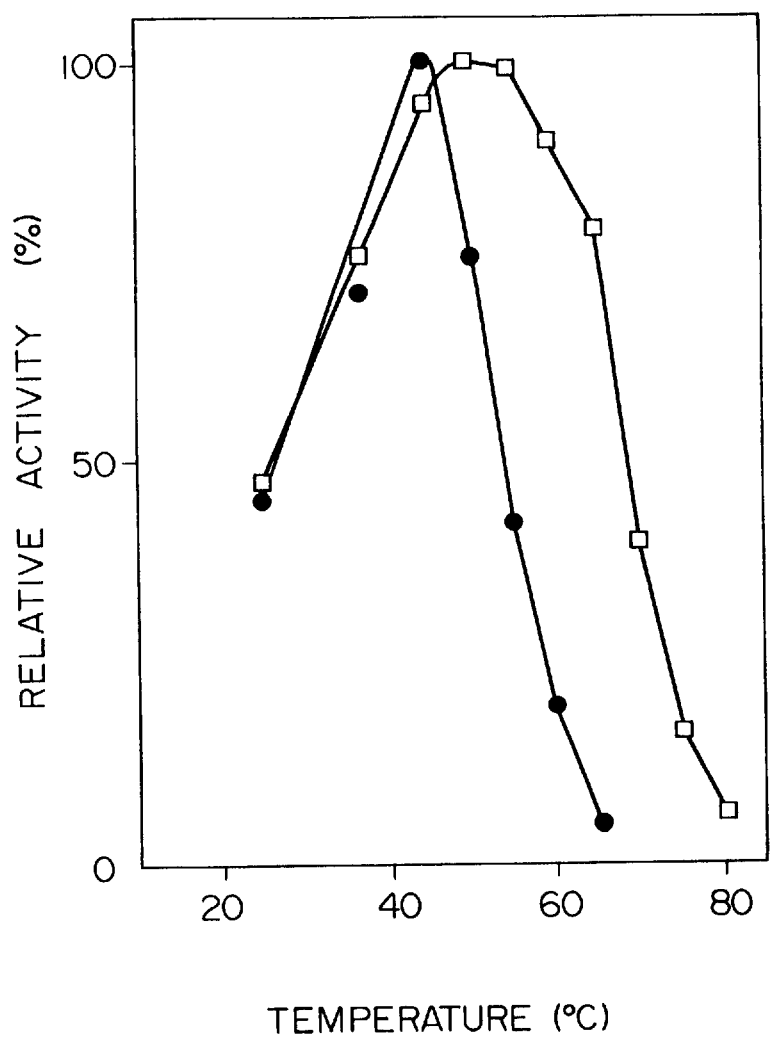
FIG. 3 is a graph showing temperature activity curves obtained in Experiment 3.

The Michaelis constant, pH stability, optimum pH and optimum temperature of the modified AOD and the intact AOD were obtained by a conventional method. The resulting Michaelis constants are shown in Table 4. The resulting pH stability is shown in FIG. 1. The resulting pH activity is shown in FIG. 2. The resulting temperature activity is shown in FIG. 3. In FIGS. 1, 2 and 3, the curve —●— means the results of the intact AOD and the curve —□— means the results of the modified AOD.

TABLE 4

| Substrate | Ascorbic acid | Oxygen |
| --- | --- | --- |
| Modified AOD | 0.26 mM | 0.098 mM |
| Intact AOD | 0.50 mM | 0.068 mM |

As is clear from the results shown in Table 4, and FIGS. 1, 2 and 3, the modified AOD has almost the same or superior fundamental properties as enzyme compared with the intact AOD.

Experiment 4
Study of Resistance to Subtilisin

Resistance to subtilisin of the modified AOD obtained in Example 1 and the intact AOD was compared.

(Procedure)

To a solution obtained by dissolving 20 μg of predetermined AOD in 1 ml of 0.1M tris(hydroxymethyl)-aminomethane.hydrochloric acid buffer solution (pH 8.0), 10 μl of a solution containing 14.4 U/ml of subtilisin (mfd. by ICN Biochemicals Co.) was added and incubated at 37° C. for a predetermined time.

A change of residual activity at the time of incubation was measured.

(Results)

The results are shown in Table 5. In Table 5, the figures mean the residual activity after the treatment with subtilisin, when the AOD activity immediately after the preparation of AOD solution is taken as 100.

TABLE 5

| Treating time (min.) | Residual activity (%) | |
| --- | --- | --- |
| | Modified AOD | Intact AOD |
| 0 | 100 | 100 |
| 5 | 91.0 | 42.2 |
| 25 | 87.6 | 33.5 |
| 90 | 86.0 | 28.5 |
| 150 | 82.3 | 23.1 |

As is clear from the results of Table 5, the modified AOD of the present invention is remarkably improved in resistance to subtilisin compared with the intact AOD.

Resistance to proteases other than subtilisin such as trypsin, papain, chymotrypsin, and thermolysin was also examined. Both the modified AOD and the intact AOD were stable to these proteases.

EXAMPLE 2
Preparation of Modified GK (1) In 4 ml of 0.2M pyrophosphate buffer solution (pH 10.0), 200 mg of dextran (molecular weight 69,000) was dissolved. While maintaining the pH of the resulting solution at 8 to 9 using a pH-stat, 440 mg of succinic anhydride was added to the solution gradually. Then, the reaction was continued at room temperature for 2 hours with stirring. The resulting reaction solution was place in a dialysis tube and dialyzed against pure water (1 liter×5 times) to obtain succinic acid-modified dextran. The amount of carboxyl group in the resulting succinic acid-modified dextran was 1.6 per glucose residue constituting the succinic acid-modified dextran.

(2) In 1 ml of 10 mM phosphate buffer solution (pH 5.5), 10 mg of GK (mfd. by Toyobo Co., Ltd., derived from *Cellulomonas sp.*) was dissolved. The resulting solution was dialyzed against the phosphate buffer solution several times. The resulting solution was added to a solution obtained by adding 10 mg of WSC to 6 ml of 10 mM phosphate buffer solution containing 10 mg of the succinic acid-modified dextran obtained in (1) mentioned above with stirring, followed by reaction at room temperature for 2 hours. The resulting reaction solution was packed in a dialysis tube and dialyzed against 50 mM Tris buffer solution (pH 8.0) to obtain the desired modified GK (enzyme activity recovery 27.2%).

Experiment 5
Study of Thermal Stability

Thermal stability of the modified GK obtained in Example 2 and the intact GK was compared.

(Procedure)

A solution obtained by dissolving a predetermined GK so as to make the amount 1 U/ml in 20 mM phosphate buffer solution (pH 7.0) and incubated at 55° C. or 60° C. to assay the GK activity after a predetermined time. Based on the assayed values, a regression line showing a relationship between a time elapsed and a logarithm of GK activity at each time was obtained, and the gradient of regression line was defined as a first-order rate constant of thermoinactivation.

(Results)

The results are shown in Table 6.

TABLE 6

| Treating temperature (°C.) | First-order rate constant of thermoinactivation (min$^{-1}$) | |
| --- | --- | --- |
| | Modified GK | Intact GK |
| 55 | 0.0084 | 0.078 |
| 60 | 0.015 | 0.24 |

As is clear from the results of Table 6, the modified GK of the present invention is remarkably improved in the thermal stability compared with the intact GK.

Further, the modified GK obtained in Example 2 and the intact GK were dissolved in 20 mM phosphate buffer solution (pH 7.0) so as to make the amount 1 U/ml and stored at 4° C. for predetermined days to measure the GK activity.

The results are shown in Table 7, wherein the figures mean the residual activity after predetermined days when the GK activity immediately after the preparation of GK solution is taken as 100.

TABLE 7

| Storing days | Residual activity (%) | |
| --- | --- | --- |
| | Modified GK | Intact GK |
| 20 | 95.8 | 78.0 |
| 40 | 88.1 | 69.4 |

TABLE 7-continued

| | Residual activity (%) | |
|---|---|---|
| Storing days | Modified GK | Intact GK |
| 60 | 81.3 | 62.6 |
| 80 | 75.5 | 58.0 |

As is clear from the results of Table 7, the modified GK of the present invention is remarkably improved in stability in the aqueous solution compared with the intact GK.

EXAMPLE 3
Preparation of Modified AOD (1) To 11 ml of 0.2M N,N-bis(2-hydroxyethyl)-2-aminoethanesulfonate (BES) buffer solution (pH 7.5) containing 260 mg of dialdehyde form dextran (molecular weight 100,000) obtained by oxidation with meta-periodic acid according to the method described in Proceedings National Academy Science USA, vol. 73, page 2128, 1976, 1 g of 6-aminocaproic acid was added, followed by stirring at room temperature for 24 hours. To the resulting reaction solution, 50 mg of sodium borohydride was added and reacted. Then, the resulting solution was placed in a dialysis tube and dialyzed against pure water (1 liter×5 times) to give 6-aminocaproic acid-modified dextran. The amount of carboxyl group in the resulting 6-aminocaproic acid-modified dextran was 0.3 per glucose residue constituting the 6-aminocaproic acid-modified dextran.

(2) To 1 ml of an aqueous solution containing 10 mg of the 6-aminocaproic acid-modified dextran obtained in (1) mentioned above, 40 mg of WSC and 10 mg of AOD (mfd. by Eastman Kodak Co., derived from pumpkin) were added, followed by reaction at 10° C. for 1 hour while maintaining the pH at 5.0 using a pH-stat. The resulting reaction solution was packed in a dialysis tube and dialyzed against a 10 mM phosphate buffer solution (pH 7.0) to give the desired modified AOD (enzyme activity recovery 49.1%).

Experiment 6
Study of Thermal Stability

The modified AOD obtained in Example 3 and the intact AOD were compared in thermal stability.

(Procedure)

A solution obtained by dissolving a predetermined AOD in an amount of 4 U/ml in 20 mM phosphate buffer solution (pH 7.0) was incubated at 45° C., 56° C. or 60° C. and subjected to measurement of AOD activity after a period of predetermined time. Based on the measured values, a regression line showing a relationship between a time elapsed and logarithms of AOD activity at each time was obtained, and the gradient of regression line was defined as a first-order rate constant of thermoinactivation.

(Results)
The results are shown in Table 8.

TABLE 8

| Treating temperature | First-order rate constant of thermoinactivation | |
|---|---|---|
| (°C.) | Modified AOD | Intact AOD |
| 45 | $1.9 \times 10^{-4}$ | $8.5 \times 10^{-4}$ |
| 56 | $1.0 \times 10^{-3}$ | $1.3 \times 10^{-2}$ |
| 60 | $2.0 \times 10^{-3}$ | — |

As is clear from the results of Table 8, the modified AOD of the present invention is remarkably improved in the thermal stability compared with the intact AOD.

EXAMPLE 4
Preparation of Modified GOD (1) To a solution obtained by dissolving 1 g of pullulan (molecular weight 200,000) in 70 ml of aqueous solution of 2M sodium carbonate, 1 ml of accetonitrile containing 1 g of bromine cyanide was added and reacted for 2 minutes. The reaction solution was dialyzed against an aqueous solution of 0.1M sodium bicarbonate (containing 0.5M sodium chloride). To the resulting activated pullulan solution, 6 g of 5-aminovaleric acid was added and reacted at 4° C. overnight, followed by dialysis against water to give 5-aminovaleric acid-modified pullulan. The amount of carboxyl group in the obtained 5-aminovaleric acid-modified pullulan was 0.2 per glucose residue constituting the 5-aminovaleric acid-modified pullulan.

(2) A solution obtained by dissolving 15 mg of GOD (mfd. by Toyobo Co., Ltd., derived from Aspergillus niger) in 10 mM phosphate buffer solution (pH 7.0) was added to a solution obtained by adding 10 mg of WSC to 6 ml of 20 mM phosphate buffer solution containing 10 mg of the 5-aminovaleric acid-modified pullulan obtained in (1) mentioned above, and reacted at 4° C. for 24 hours. The resulting reaction mixture was desalted with column chromatography [filler Sephadex G-25, a trade name, mfd. by Pharmacia; eluent 10 mM acetate buffer solution (pH 5.5)] to give the desired modified GOD (enzyme activity recovery 72.0%).

Experiment 7
Study of Thermal Stability

Thermal stability of the modified GOD obtained in Example 4 was compared with the intact GOD.

(Procedure)

A solution obtained by dissolving 1.5 U/ml of a predetermined GOD in 20 mM phosphate buffer solution (pH 7.0) was incubated at 60° C. and subjected to measurement of GOD activity after a predetermined time. Based on measured values, a regression line showing a relationship between a time elapsed and logarithms of GOD activity at each time was obtained. The gradient of the regression line was defined as a first-order rate constant of thermoinactivation.

(Results)
The results are shown in Table 9.

TABLE 9

| Treating temperature | First-order rate constant of thermoinactivation | |
|---|---|---|
| (°C.) | Modified GOD | Intact GOD |
| 60 | 0.012 | 0.25 |

As is clear from the results of Table 9, the modified GOD of the present invention is remarkably improved in thermal stability compared with the intact GOD.

EXAMPLE 5
Preparation of Modified COD

The process of Example 1(1) was repeated except for using 1 g of Ficoll (molecular weight 400,000) in place of using the dextran to give a pyromellitic acid-modified Ficoll. To 2.7 ml of water containing 5 mg of the pyromellitic acid-modified Ficoll, 65 mg of WSC was added. To the resulting solution maintained at pH 7.0 using a pH-stat, 0.5 ml of 10 mM phosphate buffer solution (pH 7.0) containing 5 mg of COD (mfd. by Toyo Jozo Co., Ltd., derived from *Arthrobactor sp.*) was added and reacted at 4° C. for 17 hours. The resulting reaction solution was dialyzed against 10 mM Tris(hydroxymethyl)-aminomethane.hydrochlorate buffer solution (pH 8.0) to give the desired modified COD (enzyme activity recovery 51.7%).

Experiment 8
Study of Thermal Stability

Thermal stability of the modified COD obtained in Example 5 and the intact COD was compared.

(Procedure)

A solution obtained by dissolving 1 U/ml of a predetermined COD in 20 mM phosphate buffer solution (pH 7.0) was incubated at a predetermined temperature and subjected to measurement of COD activity after a predetermined time. Based on the measured values, a regression line showing a relationship between a time elapsed and logarithms of COD activity at each time was obtained. The gradient of the regression line was defined as a first-order rate constant of thermoinactivation.

(Results)

The results are shown in Table 10.

As is clear from the results of Table 10, the modified COD of the present invention is remarkably improved in thermal stability compared with the intact COD.

TABLE 10

| Treating temperature (°C.) | First-order rate constant of thermoinactivation | |
| --- | --- | --- |
| | Modifed COD | Intact COD |
| 40 | $8.1 \times 10^{-4}$ | $1.3 \times 10^{-2}$ |
| 45 | $2.8 \times 10^{-3}$ | $1.5 \times 10^{-1}$ |
| 50 | $4.4 \times 10^{-3}$ | — |
| 54 | $2.5 \times 10^{-2}$ | — |
| 60 | $1.4 \times 10^{-1}$ | — |

Experiment 9
Study of Storage Stability in Solution

Storage stability in a solution of the modified COD obtained in Example 5 and the intact COD was compared.

(Procedure)

A solution obtained by dissolving 1.5 U/ml of a predetermined COD in 50 mM 3-(N-morpholino)propanesulfonate (MOPS) buffer solution (pH 7.7) was stored at a predetermined temperature for a predetermined time to measure the change of COD activity.

(Results)

The results are shown in Table 11, wherein the figures show COD residual activity after predetermined time, when the COD activity immediately after the preparation of the COD solution is taken as 100.

TABLE 11

| | Residual activity (%) | |
| --- | --- | --- |
| Stored days | Modified COD | Intact COD |
| 0 | 100 | 100 |
| 5 | 100 | 43.4 |
| 10 | 86.0 | 15.0 |
| 20 | 74.1 | 6.2 |
| 35 | 72.5 | 3.1 |

As is clear from the results of Table 11, the modified COD of the present invention is remarkably improved in storage stability in the solution compared with the intact COD.

Comparative Example 1
(Preparation of Crosslinked AOD)

To 1 ml of 10 mM phosphate buffer solution (pH 7.0) dissolving 4.1 mg of AOD (mfd. by Eastman Kodak Co., derived from pumpkin), 50 μl of a solution of 2.5% glutaraldehyde was added and reacted at room temperature for 3 hours stirring. After the reaction, the reaction solution was dialyzed against 20 mM phosphate buffer solution (pH 7.0) to give crosslinked AOD (enzyme activity recovery 73.4%).

(Measurement of First-order Rate Constant of Thermoinactivation))

Thermal stability of the crosslinked AOD and the intact AOD compared by means of the first-order rate constant of thermoinactivation. The measuring a procedure is as follows.

A solution obtained by dissolving 4 U/ml of a predetermined AOD in 20 mM phosphate buffer solution (pH 7.0) was incubated at a predetermined temperature, followed by measurement of AOD activity after predetermined days. Based on the measured values, a regression line showing a relationship between a time elapsed and logarithms of AOD activity at each time was obtained. The gradient of the regression line was defined as a first-order rate constant of thermoinactivation.

The results are shown in Table 12.

TABLE 12

| Treating temperature (°C.) | First-order rate constant of thermoinactivation | |
| --- | --- | --- |
| | Crosslinked AOD | Intact AOD |
| 4 | $1.4 \times 10^{-6}$ | $1.4 \times 10^{-6}$ |
| 30 | $1.4 \times 10^{-5}$ | $1.4 \times 10^{-5}$ |
| 56 | $1.3 \times 10^{-3}$ | $2.1 \times 10^{-2}$ |

As is clear from Table 12, the crosslinked AOD is remarkably improved in the storage stability in the solution at a high temperature (56° C.) compared with the intact AOD, but it is almost the same as the intact AOD in the storage stability when stored at 4° C. and 30° C.

Comparative Example 2
Preparation of Dextran-modified Glucoamylase (1) A solution in an amount of 2 ml of 0.1M acetate buffer solution (pH 5.0) containing 26 mg of dialdehyde form dextran (molecular weight 100,000) obtained by oxidation with metaperiodic acid according the method described in Proceedings National Academy Science USA, vol. 73, page 2128, 1976, and 1 ml of 50 mM acetate buffer solution (pH 5.5) containing 26 mg of glucoamylase (derived from Saccharomyces, hereinafter referred to as "GA") were mixed. To the resulting mixture, 100 μl of borane-pyridine complex was added and reacted at 37° C. for 20 hours. After the reaction, the reaction solution was dialyzed against 10 mM acetate buffer solution (pH 5.5) to give the desired modified dextran-modified GA (enzyme activity recovery 80.6%).

(2) The process of Example 1(2) was repeated except for using 10 mg of GA in place of AOD to give the desired dextran-modified GA (enzyme activity recovery 47.4%).

The stability in a solution of the dextran-modified GA obtained (1) and (2) mentioned above and the intact GA was compared.

(Procedure)

A solution obtained by dissolving 2 U/ml of a predetermined GA in 50 mM acetate buffer solution (pH 4.5) was treated at a predetermined temperature for 10 minutes to obtain the residual activity of GA.

(Results)

The results are shown in Table 13.

TABLE 13

| Enzyme | Treating temperature (°C.) | | | |
|---|---|---|---|---|
| | 50 | 55 | 60 | 65 |
| Intact GA | 100 | 66.1 | 20.0 | 0.1 |
| Comparative Example 2(1) | 87.3 | 85.9 | 56.3 | 45.9 |
| Comparative Example 2(2) | 47.4 | 3.7 | 0 | 0 |

As is clear from the results of Table 13, the stability of the dextran-modified GA obtained in the process of (2) mentioned above is worse than that of the dextran-modified GA obtained in the process (1) mentioned above.

This means that when the kind of enzyme to be treated is changed from the specific enzymes usable in the present invention, no effect is obtained (rather, a reverse effect is obtained).

Comparative Example 3

Preparation of Modified AOD by Borane-pyridine Complex Method

A 0.1M phosphate buffer solution (pH 7.5) in an amount of 0.8 ml containing 10 mg of dialdehyde form dextran (molecular weight 100,000) obtained by oxidation with metaperiodic acid according to the method described in Proceedings National Academy Science USA, vol. 73, page 2128, 1976, was mixed with 1 ml of 10 mM phosphate buffer solution (pH 7.5) containing 10 mg of AOD (mfd. by Eastman Kodak Co.). To the resulting mixture, 20 $\mu$l of borane-pyridine complex was added and reacted at room temperature for 24 hours. After the reaction, the reaction solution was dialyzed against 20 mM phosphate buffer solution (pH 7.0) to give the desired dextran-modified AOD (enzyme activity recovery 5.7%).

As is clear from the results mentioned above, the method of binding dextran to AOD using the borane-pyridine complex is so low in the enzyme activity recovery that it is not practical.

EXAMPLE 6

Preparation of Modified COD

To a solution obtained by adding 50 mg of WSC to 2 ml of 20 mM phosphate buffer solution (pH 5.5) containing 10 mg of sodium polyaspartic acid (molecular weight 16,400), 1 ml of 5 mM phosphate buffer solution (pH 7.0) containing 10 mg of COD (mfd. by Toyo Jozo Co., Ltd.) was added, followed by reaction at 4° C. for 24 hours. After the reaction, the reaction solution was dialyzed against 50 mM MOPS buffer solution (pH 7.7) to give the desired modified COD (enzyme activity recovery 63.8%).

The modified COD thus obtained and the intact COD were subjected to measurement of first-order rate constant of thermoinactivation at 56° C. in 50 mM MOPS buffer solution (pH 7.7). The results are shown in Table 14.

TABLE 14

| Treating temperature | First-order rate constant of thermoinactivation | |
|---|---|---|
| (°C.) | Modified COD | Intact COD |
| 56 | 0.046 | Deactivated completely within 1 minute. |

As is clear from the results of Table 14, the modified COD of the present invention is remarkably improved in thermal stability compared with the intact COD.

EXAMPLE 7

Preparation of Modified POD

To 2 ml of an aqueous solution containing 5 mg of pyromellitic acid-modified dextran obtained in Example 1(1), 65 mg of WSC was added. To the resulting solution maintained at pH 6.0 using a pH-stat, 0.5 ml of 10 mM phosphate buffer solution (pH 7.0) containing 5 mg of POD (mfd. by Sigma Chemical Co.) was added and reacted at 5° C. for 24 hours. The resulting reaction solution was packed in a dialysis tube and dialyzed against 20 mM phosphate buffer solution (pH 7.0) to give the desired modified POD (enzyme activity recovery 80.6%).

The thus obtained modified POD and the intact POD were dissolved in 20 mM phosphate buffer solution (pH 7.0) in predetermined concentrations, respectively, and stored at 45° C. to measure the change of residual activity. The results are shown in Table 15.

As is clear from the results of Table 15, the modified POD of the present invention is remarkably improved in thermal stability compared with the intact POD.

TABLE 15

| | Residual activity (%) | |
|---|---|---|
| Stored days | Modified POD | Intact POD |
| 18 | 49 | 31 |
| 55 | 37 | 24 |
| 78 | 24 | 10 |

EXAMPLE 8

Preparation of Modified US

To 2 ml of aqueous solution containing 5 mg of pyromellitic acid-modified dextran obtained in Example 1(1), 65 mg of WSC was added. To the resulting solution maintained at pH 6.0 using a pH-stat, 0.5 ml of 10 mM phosphate buffer solution (pH 7.0) containing 5 mg of US (mfd. by Toyobo Co., Ltd., derived from *Candida sp.*) was added and reacted at 5° C. for 24 hours. The resulting reaction solution was packed in a dialysis tube and dialyzed against 20 mM phosphate buffer solution (pH 7.0) to give the desired modified US (enzyme activity recovery 27.6%).

The thus obtained modified US and the intact US were dissolved in 20 mM phosphate buffer solution (pH 7.0) in an amount of 1 U/ml, respectively, and stored at a predetermined temperature for 30 min. to measure the change of residual activity. The results are shown in Table 16.

As is clear from the results of Table 16, the modified US of the present invention is remarkably improved in thermal stability compared with the intact US.

TABLE 16

| Predetermined temperature (°C.) | Residual activity (%) | |
|---|---|---|
| | Modified US | Intact US |
| 65 | 98 | 65 |
| 75 | 65 | 15 |
| 80 | 30 | 0 |

EXAMPLE 9
Preparation of Modified SAO

To 2 ml of aqueous solution containing 5 mg of pyromellitic acid-modified dextran obtained in Example 1(1), 65 mg of WSC was added. To the resulting solution maintained at pH 6.0 using a pH-stat, 0.5 ml of 10 mM phosphate buffer solution (pH 7.0) containing 10 mg of SAO (mfd. by Toyobo Co., Ltd., derived from *Arthrobactor sp.*) was added and reacted at 5° C. for 24 hours. The resulting reaction solution was packed in a dialysis tube and dialyzed against 20 mM phosphate buffer solution (pH 7.0) to give the desired modified SAO (enzyme activity recovery 19.5%).

The thus obtained modified SAO and the intact SAO were dissolved in 20 mM phosphate buffer solution (pH 7.0) in an amount of 20 U/ml, respectively, and stored at a predetermined temperature for 30 min. to measure the change of residual activity. The results are shown in Table 17.

As is clear from the results of Table 17, the modified SAO of the present invention is remarkably improved in thermal stability compared with the intact SAO.

TABLE 17

| Predetermined temperature (°C.) | Residual activity (%) | |
|---|---|---|
| | Modified SAO | Intact SAO |
| 40 | 100 | 78 |
| 45 | 100 | 35 |
| 50 | 99 | 0 |

EXAMPLE 10
Preparation of Modified XOD

To 2 ml of aqueous solution containing 5 mg of pyromellitic acid-modified dextran obtained in Example 1(1), 65 mg of WSC was added. To the resulting solution maintained at pH 6.0 using a pH-stat, 0.5 ml of 10 mM phosphate buffer solution (pH 7.0) containing 10 mg of XOD (mfd. by Boehringer Mannheim GmbH., derived from cow milk) was added and reacted at 50° C. for 24 hours. The resulting reaction solution was packed in a dialysis tube and dialyzed against 20 mM phosphate buffer solution (pH 7.0) to give the desired modified XOD (enzyme activity recovery 24.0%).

The thus obtained modified XOD and the intact XOD were dissolved in 20 mM phosphate buffer solution (pH 7.0) in an amount of 0.2 U/ml, respectively, and stored at a predetermined temperature for 75 min. to measure the change of residual activity. The results are shown in Table 18.

As is clear from the results of Table 18, the modified XOD of the present invention is remarkably improved in thermal stability compared with the intact XOD.

TABLE 18

| Predetermined temperature (°C.) | Residual activity (%) | |
|---|---|---|
| | Modified XOD | Intact XOD |
| 56 | 75.6 | 40.5 |
| 58 | 60.0 | 31.2 |
| 60 | 53.5 | 23.4 |

EXAMPLE 11
Preparation of Modified AOD (1) In 5 ml of 0.27 pyrophosphate buffer solution (pH 9.0), 0.1 g of α-, β- or γ-cyclodextrin (mfd. by Wako Pure Chemical Industries, Ltd.) was dissolved. To the resulting solution, 0.5 g of pyromellitic anhydride was added gradually while maintaining the pH of the solution at 8 to 9 using a pH-stat. Then, the reaction was continued at room temperature with stirring for 2 hours. The resulting solution was desalted by column chromatography [filler: Sephadex G-25, mfd. by Pharmacia; eluent: water] to give pyromellitic acid-modified α-, β- and γ-cyclodextrin.

(2) A solution obtained by dissolving 10 mg of AOD (mfd. by Boehringer Mannheim GmbH, derived from pumpkin) in 1 ml of 5 mM phosphate buffer solution (pH 6.0) was dialyzed against the phosphate buffer solution several times. The resulting solution was added to a solution obtained by adding 100 mg of WSC to 5 ml of 20 mM phosphate buffer solution containing 10 mg of pyromellitic acid-modified α-, β- or γ-cyclodextrin [hereinafter referred to as "PM-α-CD, PM-β-CD and PM-γ-CD, respectively] obtained in (1) mentioned above with stirring, followed by reaction at 5° C. for 24 hours. The resulting reaction solution was placed in a dialysis tube and dialyzed against 20 mM phosphate buffer solution (pH 7.0) to obtained the desired modified AOD. The enzyme activity recovery was as follows:

| | |
|---|---|
| PM-α-CD-modified AOD | 32.5% |
| PM-β-CD-modified AOD | 31.6% |
| PM-γ-CD-modified AOD | 31.2% |

When the resulting modified AOD was analyzed by using high-pressure liquid chromatography (HPLC), individual molecular weights were about 400,000. Further, unreacted AOD was hardly observed.

Experiment 10
Study of Thermal Stability

Thermal stability of the modified AOD obtained in Example 11 and the intact AOD was compared.

The procedure was the same as Experiment 1 except for making the treating time 35 minutes.

The results are shown in Table 19.

TABLE 19

| Treating temperature (°C.) | Residual activity (%) | | | |
|---|---|---|---|---|
| | Intact AOD | PM-α-CD-modified AOD | PM-β-CD-modified AOD | PM-γ-CD-modified AOD |
| 56 | 0 | 72.7 | 70.4 | 69.5 |
| 61 | 0 | 86.3 | 78.5 | 76.2 |

As is clear from the results of Table 19, the modified AODs of the present invention are remarkably improved in thermal stability compared with the intact AOD.

Experiment 11
Study of Storage Stability in Solution

Storage stability in a solution of the modified AODs obtained in Example 11 and the intact AOD was compared.

(Procedure)

In 20 mM phosphate buffer solution (pH 7.0), predetermined AOD was dissolved so as to make the amount 5 U/ml, and stored at 30° C. for predetermined days. A change of AOD activity was measured.

(Results)

The results are shown in Table 20, wherein the figure mean residual activity after predetermined days when AOD activity immediately after the preparation of AOD solution is taken as 100.

TABLE 20

| | Residual activity (%) | | | |
|---|---|---|---|---|
| Stored days | Intact AOD | PM-α-CD-modified AOD | PM-β-CD-modified AOD | PM-γ-CD-modified AOD |
| 7 | 89.3 | 98.7 | 101.0 | 100 |
| 14 | 74.4 | 96.0 | 93.0 | 93.8 |
| 21 | 66.6 | 84.2 | 85.9 | 83.5 |
| 32 | 55.3 | 81.3 | 80.7 | 79.9 |

As is clear from the results of Table 20, the storage stability in the solution of the modified AODs of the present invention is remarkably improved compared with the intact AOD.

EXAMPLE 12

In 20 mM phosphate buffer solution (pH 6.0), each 10 mg of sodium heparin (mfd. by Wako Pure Chemical Industries, Ltd.), pectic acid (mfd. by Wako Pure Chemical Industries, Ltd.) or ethylene-maleic acid copolymer (hereinafter referred to as "EMAC", mfd. by Aldrich Chemical Co.) was dissolved. To this, 100 mg of WSC was added, followed by addition of a solution obtained by dissolving 10 mg of AOD (mfd. by Boehringer Mannheim GmbH, derived from pumpkin) in 1 ml of 5 mM phosphate buffer (pH 6.0) and reaction at room temperature for 6 hours. The resulting reaction solution was packed in a dialysis tube and dialyzed against a 20 mM phosphate buffer solution (pH 7.0) to give the desired modified AOD.

The activity recoveries of AODs are shown in Table 21. When the resulting modified AODs were analyzed by using high-pressure liquid chromatography (HPLC), the molecular weights are about 400,000 to 600,000, respectively. Further, unreacted AOD was hardly observed.

TABLE 21

| | Activity recovery (%) |
|---|---|
| Heparin-modified AOD | 35.9 |
| Pectic acid-modified AOD | 42.6 |
| EMAC-modified AOD | 33.8 |

Experiment 12
Study of Thermal Stability

Thermal stability of the modified AODs obtained in Example 12 and the intact AOD was compared.

The procedure was the same as Experiment 1 except for making the treating time 35 minutes.

The results are shown in Table 22.

TABLE 22

| | Residual activity (%) | | | |
|---|---|---|---|---|
| Treating temperature (°C.) | Intact AOD | Heparin-modified AOD | Pectic acid-modified AOD | EMAC-modified MOD |
| 56 | 0 | 65.6 | 89.9 | 75.8 |
| 61 | 0 | 19.7 | 13.7 | 63.6 |

As is clear from the results of Table 22, the modified AODs of the present invention are remarkably improved in thermal stability compared with the intact AOD.

Experiment 13
Study of Storage Stability in Solution

Storage stability in a solution of the modified AODs obtained in Example 12 and the intact AOD was compared.

(Procedure)

In 20 mM phosphate buffer solution (pH 7.0), predetermined AOD was dissolved so as to make the amount 5 U/ml, and stored at 30° C. for predetermined days. A change of AOD activity was measured.

(Results)

The results are shown in Table 23, wherein the figures mean residual activity after predetermined days when AOD activity immediately after the preparation of AOD solution is taken as 100.

TABLE 23

| | Residual Activity (%) | | | |
|---|---|---|---|---|
| Stored days | Intact AOD | Heparin-modified AOD | Pectic acid-modified AOD | EMAC modified AOD |
| 7 | 89.3 | 95.9 | 97.6 | 100 |
| 14 | 74.4 | 89.2 | 90.6 | 100 |
| 21 | 66.6 | 76.2 | 80.0 | 93.4 |
| 32 | 55.3 | 69.7 | 70.5 | 85.8 |

As is clear from the results of Table 23, the storage stability in the solution of the modified AODs of the present invention is remarkably improved compared with the intact AOD.

As mentioned above, the modified enzyme of the present invention has almost the same fundamental properties for enzymatic reaction such as Km values, optimum pH range, etc. as the starting enzyme, and is remarkably improved in resistance to heat, proteases, denaturants and in storage stability in an aqueous solution compared with the intact enzyme. It is very advantageous in this art that hydrogen peroxide generating enzymes, AOD, POD, URS, CAT and GK can be modified to provide the above-mentioned properties.

What is claimed is:

1. A heat stable and Water soluble modified enzyme consisting essentially of
   uricase modified by reacting 0.1 to 10 weight parts of uricase with 1 weight part of a polyamino acid containing 25% or more of glutamic acid or aspartic acid residues through forming carboxylic acid amide linkage between the amino groups of uricase and the carboxylic acid groups of the polyamino acid.

2. The modified enzyme according to claim 1, wherein the modified enzyme is obtained by reacting the amino groups of uricase with the polyamino acid containing glutamic acid or aspartic acid residues.

3. The modified uricase according to claim 1, wherein the compound capable of binding a carboxyl group and an amino group is carbodiimide or a derivative thereof selected from the group consisting of dicyclohexylcarbodiimide, di-p-toluoylcarbodiimide, benzyldimethylaminopropylcarbodiimide, and 1-ethyl-3-(3-dimethylaminopropyl)carbodiimide.

4. A heat stable and water soluble modified enzyme selected from the group consisting of choline oxidase, glucose oxidase, xanthine oxidase, oxalate oxidase, sarcosine oxidase, ascorbate oxidase, urease, catalase and glycerokinase, said enzyme modified by reacting 0.1 to 10 weight parts of the enzyme with 1 weight part of a) a polysaccharide having a molecular weight of 4,000 to 10,000,000 and containing 0.1 to 5 carboxyl groups per sugar unit of the polysaccharide, or b) a polyamino acid containing 25% or more of glutamic acid or aspartic acid residues through forming carboxylic acid amide linkage between the amino groups of the enzyme and the carboxcylic acid groups of the polysaccharide or the polyamino acid.

5. The modified enzyme according to claim 4, wherein the modified enzyme is obtained by reacting the amino groups of the enzyme with the polysaccharide having carboxyl groups or with the polyamino acid containing glutamic acid or aspartic acid residues.

6. The modified enzyme according to claim 4, wherein the modified enzyme is obtained by reacting the amino groups of the enzyme with the polysaccharide having carboxyl groups.

7. The modified enzyme according to claim 6 wherein the polysaccharide having carboxyl groups is obtained by reacting a polysaccharide with an acid anhydride.

8. The modified enzyme according to claim 4, wherein the compound capable of binding a carboxyl group and an amino group is carbodiimide or a derivative thereof selected from the group consisting of dicyclohexylcarbodiimide, di-p-toluoylcarbodiimide, benzyldimethylaminopropylcarbodiimide, and 1-ethyl-3-(3-dimethylaminopropyl)carbodiimide.

* * * * *